USO05760015A

United States Patent [19]
Joullié et al.

[11] Patent Number: 5,760,015
[45] Date of Patent: Jun. 2, 1998

[54] CYCLODEXTRIN COMPOUNDS AND METHODS OF MAKING AND USE THEREOF

[75] Inventors: Madeleine M. Joullié, Philadelphia; Paul B. Weisz, State College, both of Pa.

[73] Assignee: The Trustees of the University of Pennsylvania, Philadelphia, Pa.

[21] Appl. No.: 416,107

[22] Filed: Apr. 3, 1995

Related U.S. Application Data

[63] Continuation-in-part of Ser. No. 345,011, Nov. 23, 1994, Pat. No. 5,658,894, which is a continuation of Ser. No. 900,592, Jun. 18, 1992, abandoned, which is a continuation-in-part of Ser. No. 480,407, Feb. 15, 1990, Pat. No. 5,183,809, and a continuation of Ser. No. 790,592, Nov. 12, 1991, abandoned, which is a continuation of Ser. No. 691,168, Apr. 24, 1991, abandoned, which is a continuation-in-part of Ser. No. 434,659, Nov. 9, 1989, Pat. No. 5,019,562, which is a continuation of Ser. No. 295,638, Jan. 10, 1989, abandoned, which is a continuation-in-part of Ser. No. 145,407, Jan. 19, 1988, abandoned.

[51] Int. Cl.$^6$ ............. A61K 31/715; C08B 37/16; C08B 37/00
[52] U.S. Cl. ............. 514/58; 536/103; 536/124
[58] Field of Search ............. 514/58; 536/103, 536/124

[56] References Cited

U.S. PATENT DOCUMENTS

| | | | |
|---|---|---|---|
| 3,420,788 | 1/1969 | Solms | 524/48 |
| 4,020,160 | 4/1977 | Bernstein et al. | 424/180 |
| 4,066,829 | 1/1978 | Nair et al. | 536/103 |
| 4,247,535 | 1/1981 | Lewis et al. | 424/180 |
| 4,258,180 | 3/1981 | Lewis et al. | 536/112 |
| 4,383,992 | 5/1983 | Lipari | 424/238 |
| 4,582,900 | 4/1986 | Brandt et al. | 536/103 |
| 4,596,795 | 6/1986 | Pitha | 514/58 |
| 4,727,064 | 2/1988 | Pitha | 514/58 |
| 4,764,604 | 8/1988 | Müller | 536/103 |
| 4,834,985 | 5/1989 | Elger et al. | 424/488 |
| 4,840,941 | 6/1989 | Ueno et al. | 514/59 |
| 4,877,774 | 10/1989 | Pitha et al. | 514/26 |
| 4,877,778 | 10/1989 | Carpenter et al. | 514/58 |
| 4,902,788 | 2/1990 | Zemel et al. | 536/123.1 |
| 4,929,602 | 5/1990 | Harker et al. | 514/18 |
| 5,019,562 | 5/1991 | Folkman et al. | 514/58 |
| 5,441,944 | 8/1995 | Weisz et al. | 514/58 |
| 5,464,827 | 11/1995 | Soll | 514/58 |

FOREIGN PATENT DOCUMENTS

| | | |
|---|---|---|
| 0 121 777 | 10/1984 | European Pat. Off. |
| 0 188 821 | 7/1986 | European Pat. Off. |
| 0 193 850 | 9/1986 | European Pat. Off. |
| 0 325 199 | 7/1989 | European Pat. Off. |
| 0 447 171 | 9/1991 | European Pat. Off. |
| 50-36422 | 4/1975 | Japan |
| 50-140476 | 11/1975 | Japan |
| 62-123196 | 6/1987 | Japan |
| 63-122701 | 5/1988 | Japan |
| 1 315401 | 12/1989 | Japan |
| WO 85/02767 | 7/1985 | WIPO |
| WO 87/05808 | 10/1987 | WIPO |
| WO 89/06536 | 7/1989 | WIPO |

OTHER PUBLICATIONS

Pow et al., *Low Molecular Weight Heparin Reduces Restenosis After Experimental Angioplasty, Circulation*, supp. II, vol. 80, No. 4 (Oct. 1989).
Croft et al., *Tetrahedron*, vol. 39, pp. 1417–1474 (1983).
LeVeen et al., *Investigative Radiology*, 17:470–475 (1982).
Nakashima et al., *Antimicrobial Agents and Chemotherapy*, pp. 1524–1528 (1987).
Uekama et al., *International Journal of Pharmaceutics*, vol. 10, pp. 1–15 (1982).
J. Pitha et al., *Journal of Pharmaceutical Sciences*, vol. 75(2), pp. 165–167 (1986).
Yamamoto et al., *International Journal of Pharmaceutics*, vol. 49, pp. 163–171 (1989).
*Chemical Abstracts*, 96:218351u (1982).
Fenyvesi et al., *Chem. Pharm. Bull.*, vol. 32(2), pp. 665–669 (1984).
Fenyvesi et al., *Chem. Pharm. Bull.*, vol. 32(2), pp. 670–677 (1984).
Komiyama et al., *Polymer Journal*, vol. 18(4), pp. 375–377 (1986).
Herrmann, H.C., *Abstracts of Papers*, National Meeting of the American Heart Association, Anaheim, CA; Nov. 11–14, 1991.
*Chemical Abstracts* 83:79544a (1975).
Pierce et al., *J. Cell Biochem.*, 45:319–326, 1991.
Antoniades et al., *Proc. Natl. Acad. Sci. USA*, 88: 565–569, 1991.
Lobb, *Eur. J. Clin. Invest.*, 18:321–328, 1988.
Folkman and Klagburn, *Science*, 235:442–447, 1977.
Crum, R., "A New Class of Steroids Inhibits Angiogenesis in the Presence of Heparin or a Heparin Fragment," 20 Dec. 1985, *Science*, vol. 230, pp. 1376–1378.
Folkman, J., et. al., "Control of Angiogenesis with Synthetic Heparin Substitutes," 17 Mar. 1989, *Science*, vol. 243, pp. 1490–1493.
Lobb, R.R., "Clinical Applications of Heparin–Binding Growth Factors," 1988, European Journal of clinical Investigation, vol. 18, pp. 321–336.
Antoniades, Harry N., et. al., "Injury Induces in Vivo Expression of Platelet–Derived Growth Factor (PDGF) and PDGF Receptor mRNAs in Skin Epithelial Cells and PDGF mRNA in Connective Tissue Fibroblasts," Jan. 1991, Proc. Natl. Acad. Sci. USA, vol. 88, pp. 565–569.
International Search Report, International Patent Application No. PCT/US92/09754, Jan. 26, 1993.
International Preliminary Examination Report, International Patent Appln. No. PCT/US92/09754, Feb. 10, 1994.

*Primary Examiner*—Kathleen K. Fonda
*Attorney, Agent, or Firm*—Panitch Schwarze Jacobs & Nadel, P.C

[57] ABSTRACT

The present invention provides polyanionic, substituted CDs having cellular growth modulating activity. The invention further provides CDs having anionic groups on one side of the CD molecule. Therapeutic methods for using, as well as methods of making the CD compounds of the invention, are also disclosed herein.

37 Claims, 5 Drawing Sheets

- ● ANTI-ANGIOGENESIS (W/h-CORTISONE) [% INHIBITION IN CAM]
- ○ ENDOTHELIAL CELL YEILD (CULTURE) [ΔABSORBANCE/100μl]
- × SMOOTH MUSCLE CELL INHIBITION (CULTURE) [1/(mg/ml) FOR 50% INHIB.]
- △ INHIBITION OF CELL INVASION BY HIV-1 VIRUS [1/mM FOR EFF. INHIBITION]

COMPOUND A:  R =  $-S-CH_2-CH_3$

COMPOUND B:  R =  $-S-(CH_2)7-CH_3$

COMPOUND C:  R =  $-S-(CH_2)4-CH_3$

COMPOUND D:

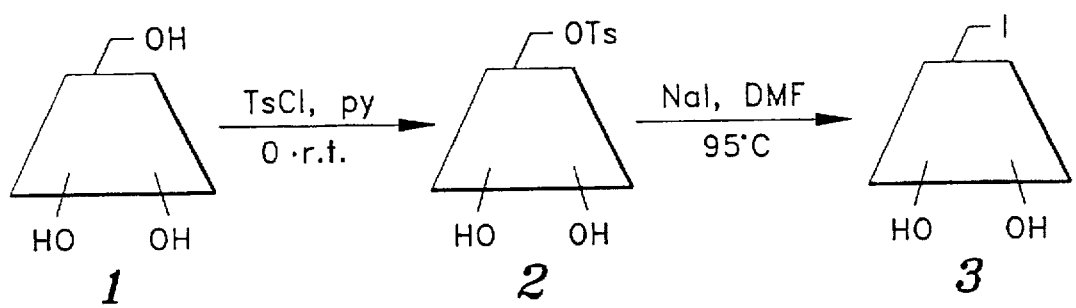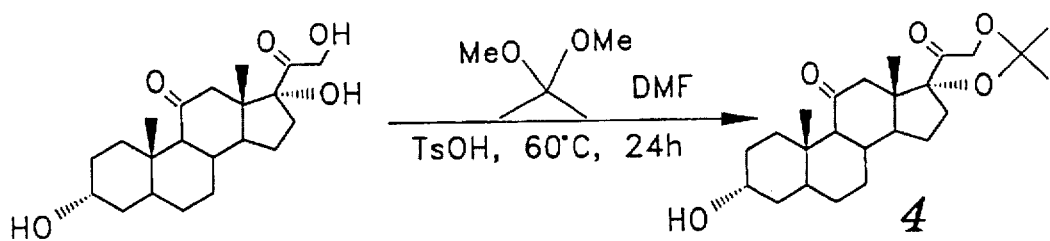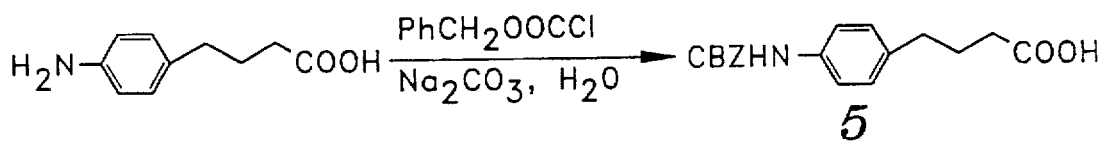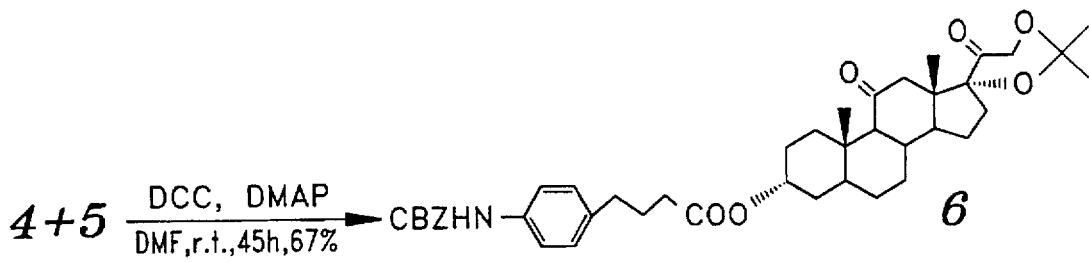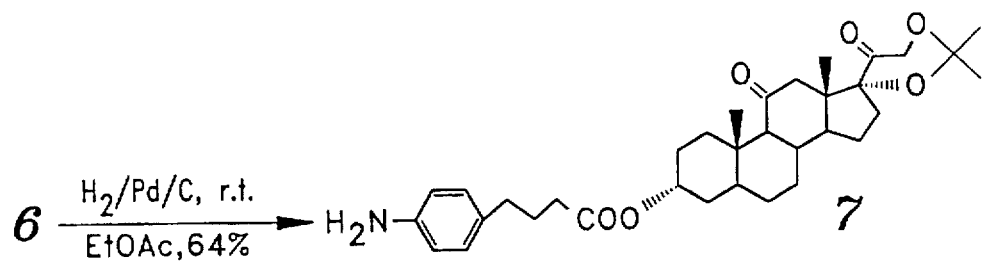
FIG. 5A
FIG. 5
FIG. 5A
FIG. 5B

CYCLODEXTRIN COMPOUNDS AND METHODS OF MAKING AND USE THEREOF

This application is a continuation-in-part of U.S. application Ser. No. 08/345,011, filed Nov. 23, 1994, now U.S. Pat. No. 5,658,894, which is a continuation of U.S. application Ser. No. 07/900,592, filed Jun. 18, 1992 (abandoned), which is a continuation-in-part of U.S. application Ser. No. 07/480,407, filed Feb. 15, 1990, now U.S. Pat. No. 5,183, 809, and a continuation of U.S. application Ser. No. 07/790, 592, filed Nov. 12, 1991 (abandoned), which is a continuation of U.S. application Ser. No. 07/691,168, filed Apr. 24, 1991 (abandoned), which is a continuation-in-part of U.S. application Ser. No. 07/434,659, filed Nov. 9, 1989, now U.S. Pat. No. 5,019,562, which is a continuation of U.S. application Ser. No. 07/295,638, filed Jan. 10, 1989 (abandoned), which a continuation-in-part of U.S. application Ser. No. 07/145,407, filed Jan. 19, 1988 (abandoned). The above-referenced patents and patent applications are incorporated herein by reference.

1. FIELD OF THE INVENTION

This invention relates to highly anionic cyclodextrin compounds having attached additional substituents with hydrophobic properties. More particularly, it is also directed to physiologically acceptable compositions comprising such compounds, and to methods of use for modulating cellular growth activity.

2. BACKGROUND OF THE INVENTION

2.1 Heparin and Its Cell Modulating Properties

It has become increasingly evident that a class of biological activities of heparin exists that is distinct from those of the classical anticoagulant properties that have long been associated with heparin. It involves various types of interaction with proteinic factors and the modulation of proliferative and other behavior of cells. Heparin interacts chemically by complex formation with growth factor proteins (heparin binding growth factors, HBGF'S) such as FGF (see e.g. Y. Shing, J. Folkman, R. Sullivan, C. Butterfield, J. Murray, and M. Klagsbrun, Science 223, 1296–1299, 1984; M. Klagsbrun and Y. Shing, *Proc. Natl. Acad. Sci. USA* 82, 805–809 1985). It modulates cell metabolism in a number of ways (see e.g. A. Yayon, M. Klagsbrun, J. D. Esko, P. Leder, and D. M. Ornitz, Cell 64, 841–848, 1991). It protects growth factors such as FGF against proteolytic degradation (see e.g. D. Gospodarowicz and J. Chen, *J. Cell Physiol.* 128, 475–484, 1986); O. Saksela, D. Moscatelli, A. Sommer, D. B. Rifkin, *i. Cell Biol.* 107, 743–751, 1988); it promotes endothelial cell proliferation and angiogenesis (see e.g. J. Folkman, R. Langer, R. Linhardt, C. Haudenschild and S. Taylor, Science 221, 719, 1983; L. B. Castellot et al, *J. Cell. Physiology* 127, 323 1986; T. Barzu et al, *J. Cellular Physiol.* 140, 538, 1989; S. C. Thornton, S. N. Mueller, E. M. Levine, Science 222, 623–625, 1983; S. N. Mueller, K. A. Thomas, J. DiSalvo, and E. M. Levine, *J. Cell Physiol.* 149, 439–448, 1989; D. B. Volkin, P. K. Tsai, J. M. Debora, J. O. Gress, C. J. Burke, R. J. Linhardt and C. R. Middaugh, *Arch. Biochem. and Biophys.* 300, 30, 1993; S Tazawa, Y Hayakawa, T Ishikawa, K Niiya, N Sakuragawa, *Thrombosis Research* 72, 4,'31–439, 1993). Heparin also inhibits smooth muscle cell proliferation (A. Clowes and M. Karnovsky, Nature 265, 1977; J. Guyton, R. Rosenberg, A. Clowes and M. Karnovsky, *Circ. Res.* 46, 625,1980; J. Castellot Jr., i. i. Choay, J. C. Lormeau, M. Petitou, E. Sache and M. J. Karnovsky, *i.Cell Biol.* 102, 1979, 1986)). In conjunction with steroidal and other agents, heparin inhibits angiogenesis (J. Folkman, R. Langer, R. Linhardt, C. Haudenschild and S. Taylor, *Science* 221, 719, 1983; b) R. Crum, S. Szabo and J. Folkman, *Science* 230, 1375, 1985; J. K. Lee, B. Choi, R. A. Sobel, E. A. Chiocca, R. L. Martuza, *J. Neurosurg.* 73, 429, 1990). It also provides other functions of altering cell behavior such as inhibiting HIV-virus infection (M. Ito, M. Bana, A. Sato, R. Pauwels, E. DeClercq, S. Shigeta, *Antiviral Res.* 7, 361–367, 1987), and others.

Unfortunately, one is limited with respect to the utilization of heparin in a variety of therapeutic applications of the types indicated above for mainly two reasons: one is the fact that there is no strict uniformity in chemical composition between different heparin preparations. Thus, the efficacy of heparins of different origins when used to inhibit angiogenesis was shown to range from good to very poor (see J. Folkman, R. Langer, R. Linhardt, C. Haudenschild and S. Taylor, *Science* 221, 719, 1983). Moreover, one is limited in the use of heparin by the fact that it inevitably introduces the anticoagulant property which at dosages indicated for many of the potential applications would lead to complications such as bleeding, stroke, etc.

The compositional and structural characteristics of heparin required for the above-described cell modulating activities appear to be distinct from those required for its anticoagulant activities. We have sought to reduce the complexity of the heparin structure toward the simplest chemical composition required for the class of cell modulating properties, and which, at the same time, would be expected to be most compatible with the living tissue environment.

We succeeded in obtaining comparable or greater cell modulating behavior after total abandonment of the flexible, large and complex chain structure of the heparin glycosaminoglycan in favor of a simple and rigid toroid of only six to eight glucose units, namely cyclodextrin (CD), if we provided a high molecular density of anionic substituents such as a minimum number of sulfate groups, as described in U.S. Pat. No. 5,019,562 to M. I. Folkman and P. B. Weisz. This type of composition, such as a cyclodextrin polysulfate (CDS), is a "heparin mimic" that was found to control angiogenesis (J. Folkman, P. B. Weisz, M. M. Joullie, W. W. LI and W. R. Ewing, *Science*, 243, 1490, 1989), to inhibit smooth muscle cell proliferation, promote the yield of endothelial cells in culture, and inhibit HIV virus invasion of human cells (P. B. Weisz, H. C. Herrmann, M. M. Joullie, K. Kumor, E. M. Levine, E. J. Macarak, D. Weiner, Angiogenesis and GAG-Mimics, in *Angiogenesis—Key Principles-Science-Technology-Medicine*, R. Steiner, P. B. Weisz, R. Langer, Ed.s, Birkhaeuser-Springer, Basel and New York, 1992; D. B. Weiner, W. V. Williams, P. B. Weisz, M. I. Greene, *Pathobiology* 60, 206, 1992). Just as is well-known in the science and study of heparin, the sulfated cyclodextrins interact with cells through adsorption on the cell membranes, as is evidenced by their protecting cells from virus invasion (see Weiner et al, above) and from their protection of erythrocytes against destruction by hemolytic agents (P. B. Weisz et al, *Biochem. Pharm.* 45, 1011–1016, 1993).

2.2 Cyclodextrins and Their Uses in Pharmacology

Cyclodextrins (hereinafter referred to for convenience as CD or CDs for the singular and the plural, respectively) are cyclic oligosaccharides consisting of at least six glucopyranose units. Although CDs with up to twelve glucopyranose units are known, only the first three homologs have been studied extensively. These compounds have the simple, well-defined chemical structure shown in FIG. 1(A). The common designations of the lower molecular weight α-, β- and γ-CDs are used throughout this specification and will refer to the chemical structure shown in FIG. 1(A) wherein n=6, 7, or 8 glucopyranose units, respectively. The initial discovery of the CDs as degradation products of starch was made at about the turn of the century, and Schardinger showed that these compounds could be prepared by the action of *Bacillus macerans* amylase upon starch (see, e.g. French, D., Adv. Carbohyd. Chem. Biochem. 12:189–260, 1957). In older literature, the compounds are often referred to as Schardinger dextrins. They are also sometimes called cycloamyloses.

Topographically, the CDs may be represented as a torus, as shown in FIG. 1(B), the upper rim of which is lined with primary —CH$_2$OH groups, and the lower rim with secondary hydroxyl groups. Coaxially aligned with the torus is a channel-like cavity of about 5, 6 or 7.5 A.U. diameter for the α-, β- and γ-CDs, respectively. These cavities make the cyclodextrins capable of forming inclusion compounds with hydrophobic guest molecules of suitable diameters.

A reasonably large number of CD derivatives have been prepared and described in the literature. In general, these chemically modified CDs are formed by reaction of the primary or secondary hydroxyl groups attached to carbons 2, 3 or 6 [FIG. 1(A)], without disturbing the α (1→4) hemiacetal linkages. A review of such preparations is given in "Tetrahedron Report Number 147, *Synthesis of Chemically Modified Cyclodextrins*", A. P. Croft and R. A. Bartsch, Tetrahedron 39(9):1417–1474 (1983), incorporated herein by reference for background (hereinafter referred to as "Tetrahedron Report No. 147").

In particular, α-, β- and γ-CD sulfates (Na salt) are shown as Compound Nos. 207, 208, and 209 in Tetrahedron Report No. 147, (supra) Table 26, p.1456. U.S. Pat. No. 2,923,704 to Berger describes the preparation of cycloamylose sulfates. U.S. Pat. No. 4,020,160 to Berstein et al. and U.S. Pat. Nos. 4,247,535 and 4,258,180 to Lewis et al. disclose the use of the modified cyclodextrin sulfates as complement inhibitors. U.S. Pat. No. 4,383,992 to Lipari describes the preparation of a water-soluble inclusion compound of a steroid and unmodified β-cyclodextrin. U.S. Pat. No. 4,596,795 to Pitha discloses the administration (by the sublingual or buccal route) of sex hormones, particularly testosterone, progesterone and estradiol in the form of their inclusion compounds with hydroxypropyl-β-CD or poly-β-CD.

As regards applications of cyclodextrins to the field of pharmacology, there is a growing number of applications concerned with solubilization of various pharmaceutical compounds. It is based on the ability of the toroidal structure of CDs to internally accommodate a large variety of molecules by internal complex formation, provided that (1) the guest molecule or a significant portion thereof can physically fit and pass through the toroidal opening, and (2) it is sufficiently hydrophobic or lipophilic to be held there by non-covalent interaction with the equally hydrophobic structure of the internal atomic sugar skeleton of the CD. Such complexation has been utilized to internalize a large variety of pharmaceutical agents and to thus deliver them into aqueous solution when they could not otherwise be dispersed into solution due to their low solubility. Also, such internal complexation has been utilized for agents having hemolytic activity. Examples of prior art are the cyclodextrin inclusion of phenothiazine neuroleptics (see Otagiri et al, *Proc. of the First Int. Symp. on Cyclodextrins*, pp. 389398 1982; Uekama et al, *J. Pharmacodyn.* 4,142–144,1981), steroid hormones (see Uekama et al, *Int. J. Pharm.* 10, 1–15, 1982), anti-inflammatory and analgesic agents (see Lister et al, *Eur. J. of Rheum. and Inflamm.*, 12, 6–11, 1993; anti-hypoxia drugs (see Wallerstein and Cserhati, *J. Biochem. and Biophys. Methods.* 29, 49–60,1994), opioids like morphine, fofentanil and others (see Jang et al, *J. Pharm. and Exper. Therap.* 261,592–600, 1992) and very many more. While various CDs and CD-derivatives have been and are being described for a growing number of such application, it must be noted that the art does not make use of highly ionic CDs. None of the foregoing references are believed to show or make obvious applicants' invention as described and claimed further below.

2.3 Significance and Applications of Methods to Modulate Cell Proliferation

A large number of biological processes are caused by and directly concerned with events that involve or lead to a lack of or to an overexpression of cell proliferation. Obviously, in embryonic development, cell division and proliferation to a controlled degree is essential. Similarly, the healing processes, after destruction of tissue or organs, whether by injury or due to pathological causes, any reconstructive or healing processes, demand recreation of cells and cellular materials. Thus, the inducing or enhancement of cell proliferation is desired in relation to the process of wound healing. Similarly, in ischemia due to loss of active blood vessels or capillaries calls for growth and formation of new endothelial cells and endothelium. Cellular regrowth is equally sought in the practice of surgery, such as in the practice of implantation wherein the growth of cellular junctions, and accommodation and growth of new blood capillaries and vessels is important for acceptance, and where accelerated accommodation is likely to diminish immune rejection. Extraneous introduction of growth factor protein has been shown to be helpful (see Roberts and McGeachie, J. Anat.,April 169, 197–207, 1990; Stagner and Samols, *EXS* 61, 381–5, 1992) if and when it can be controllably practiced. It has become clear that growth factor proteins play a prominent if not decisive role in all such constructive (i.e. embryonic) and reconstructive processes.

In contrast to the cases above, where inducement of cell proliferation is important, natural and excessive proliferative processes rarely occur in the adult body except as a result of injury or disease. Particularly prominent is the phenomenon of neovascularization, or the induction of neovascularization known as angiogenesis. It involves the proliferation of endothelial cells that subsequently form new blood capillaries and vessels. A number of diseases are either caused or accompanied by angiogenesis. Tumor growth requires constant enlargement of the nutrient, i.e., the blood supply system. Active growth therefore requires angiogenesis. Inhibition of angiogenesis can, therefore, inhibit or terminate tumor growth. In certain diseases of the eye, uncontrolled blood vessel growth can occur across the cornea; or it can destroy the retina. Both conditions can lead to blindness if angiogenesis is not controlled. Similarly, angiogenesis accompanies rheumatoid arthritis in joints, in psoriasis, and other dermatological conditions and pathologies. Thus there is need for means and methods for controlling angiogenesis, that is controlling endothelial cell proliferation. A further example of cell proliferation is that which follows the nearly inevitable damage to the surface layer of blood vessels that occurs with angioplasty, or accompanies the accumulation of plaque in cardiovascular disease. Such conditions lead to proliferation of smooth muscle cells, that can lead to restenosis after angioplastic intervention, or to more rapid increase in the size of plaque material leading to more rapid obstruction of flow. Again, the need for inhibiting cellular growth in these conditions is relevant and urgent.

2.4 The Nature of Previously Disclosed Polyanionic (Heavily Sulfated) Cyclodextrins The usual methods of sulfation (e.g. use of chlorosulfonic acid, trimethylamine/sulfur trioxide complex or sulphur trioxide/pyridine complex) practiced in the prior art, by others (e.g. see U.S. Pat. No. 12,923,704 to L. Berger; U.S. Pat. No. 4,258,180 to A. J. Lewis) or by us (U.S. Pat. No. 5,019,562 to Folkman and Weisz; and the numerous references to authorship of Weisz with Folkman, Joullie, Weiner, Barnathan, Macarak, and others in Section 2.1 above) lead to sulfate substitution on both sides of the CD toroid. Sulfate groups are positioned at any of the (hydroxyl) positions designated by 2, 3, or 6 of the glucose rings of the CD structure. FIG. 2 illustrates this.

All publications which are referenced above are incorporated herein by reference.

3. SUMMARY OF THE INVENTION

This invention is directed to polyanionic substituted cyclodextrins (CDs) and their uses. CDs having both multiple polar or anionic substituents, as well as multiple non-polar substituents of substantial hydrophobic or lipophilic character, are provided for optimal use in treating various pathologies. Preferred CDs are what are referred to as "one-sided" anionic forms of the highly anionic substituted CD, wherein most of the anionic substituents are located on one side of the CD toroid structure. The water solubility of the compounds of the present invention can be advantageously varied from insoluble to highly soluble by varying the length of the carbon chain of the non-polar substituents.

Other aspects of the present invention are compositions containing the above-described compounds for use in a number of therapeutic methods, which methods pertain to modulating cellular growth activity, as discussed below.

The invention further provides compositions for the inhibition of cellular proliferation of smooth muscle cells, comprising (1) highly anionic substituted CDs having a sufficient number of hydrophobic substituents and (2) a physiologically acceptable delivery medium, wherein the degree of the hydrophobic character of the substituents provides improved absorption into the blood plasma, depending on the mode of delivery to mammals, including humans. Such modes of delivery include intravenous or oral delivery, injection into body fluids, tissue or organs, or topical application.

The invention also provides compositions for promoting endothelial cell growth comprising (1) highly anionic substituted CDs bearing hydrophobic substituents and (2) growth factor protein, wherein the degree of the hydrophobic character of substituents is similarly adjustable.

The invention further provides compositions for the inhibition of neovascularization and angiogenesis comprising (1) highly anionic substituted CDs having hydrophobic substituents and (2) an angiostatic steroidal or non-steroidal compound, wherein the degree of the hydrophobic character of substituents is provided to achieve improved absorption into the blood as described above.

The invention also provides angiogenesis-inhibiting compounds that are highly anionic substituted CDs having hydrophobic substituents, wherein the angiostatic compound is included as at least one of the hydrophobic substituents bonded to the CD, or, alternatively, is part of an inclusion complex with a "one-sided" polyanionic CD.

The invention furthermore advantageously provides compositions that are inclusion complexes of highly anionic substituted CDs and pharmaceutical or therapeutic agents of limited water solubility. Thereby, this invention provides methods for solubilization of a variety of pharmaceutical agents in a manner which allows greater amounts of the agent to be delivered than in the prior art. This therefore surprisingly provides more effective delivery of the included therapeutic agent directly to cell or tissue surfaces than has heretofore been achieved.

The invention further provides methods of delivery that, in regard to the number of polyanionic groups and the length of the hydrophobic substituent(s) of the compounds of the invention, optimize efficacy and dose rate requirements to accomplish the desired therapeutic objective. In addition to solubilizing and delivering pharmaceutical compounds of interest, the inclusion complexes of the present invention also provide for stabilizing these compounds from decomposition.

By providing the compounds of this invention with different degrees of hydrophobicity (lipophilic), this invention allows for improved methods of delivery. For example, depending on the nature of the target tissue, more lipophilic compounds are especially suitable for providing greater affinity to fatty tissue. Also, the ability to lower solubility in body fluids can aid in localization of the compounds, i.e. in targeting applications. Furthermore, hydrophobicity aids penetration of cell membranes, and advantageously increases absorption from oral ingestion into the bloodstream.

The invention also advantageously and surprisingly provides, through use of the compounds of this invention, methods of treatment of several pathologies that involve abnormal cell proliferation activity, such as hypercholesterolemia and the prevention of stenosis or restenosis in cardiovascular disease, or following angioplasty, as well as in angiogenic diseases such as corneal neovascularization, retinopathy, tumor growth, rheumatoid arthritis, psoriasis and other pathologies accompanied or caused by angiogenesis.

The therapeutic methods of the invention further encompass positively modulating cellular activity in such fashion for enhancing wound healing, transplantation and the revascularization of ischemic tissue.

Another aspect of the present invention is a method of making the polyanionic, substituted CD compounds. It has been advantageously discovered that the compounds possess a critical minimum number of polyanionic groups, said critical number being at least ten (10). The compounds of the invention can also be advantageously synthesized in such fashion to be of a desired water solubility, either low, intermediate, or high, based upon the carbon length of a hydrophobic substituent attached at hydroxyl positions of the CD compound which are free of anionic groups.

More particularly, the present invention provides a method of making the polyanionic, hydrophobically-substituted CD compounds, wherein the polyanionic groups are positioned substantially on one side of the CD.

By way of summary, the present invention advantageously and unexpectedly provides polyanionic, hydrophobically-substituted CDs, particularly CDs which are anionically substituted on "one-side" of the molecule, which are beneficially and surprisingly suitable for application in a wide variety of therapeutic methods.

The pharmacological activity of the compounds of the present invention provide for a method of modulating cellular behavior, which cell modulatory activity includes a) promoting endothelial cell proliferation, as occurs during the process of implant/transplant surgery or wound healing; b) inhibiting endothelial cell proliferation when in combination with an angiostatic compound such as a steroid or a retinoid, which angiostatic activity is suitable for inhibiting tumor cell growth, or inhibiting neovascularization in various angiogenic diseases, such as retinopathy or psoriasis; c) inhibiting smooth muscle cell proliferation, for instance, in various cardiovascular conditions, such as inhibiting restenosis after angioplasty; and d) promoting cell and tissue membrane stability by preventing viral infection of cells, preventing hemolysis of erythrocytes by various hemolytic agents, and preventing glomerular membrane leakage in nephrology and diabetes, or protein leakage in interstitial cystitis and inflammatory bowel disease.

Accordingly, the compounds of the present invention are advantageously and unexpectedly suitable for use in a wide variety of therapeutic applications, which use satisfies the long-felt needs described above.

4. BRIEF DESCRIPTION OF THE FIGURES

The present invention may be more fully understood by reference to the following detailed description of the invention, examples and specific embodiments of the invention and figures in which.

Figure 3A:
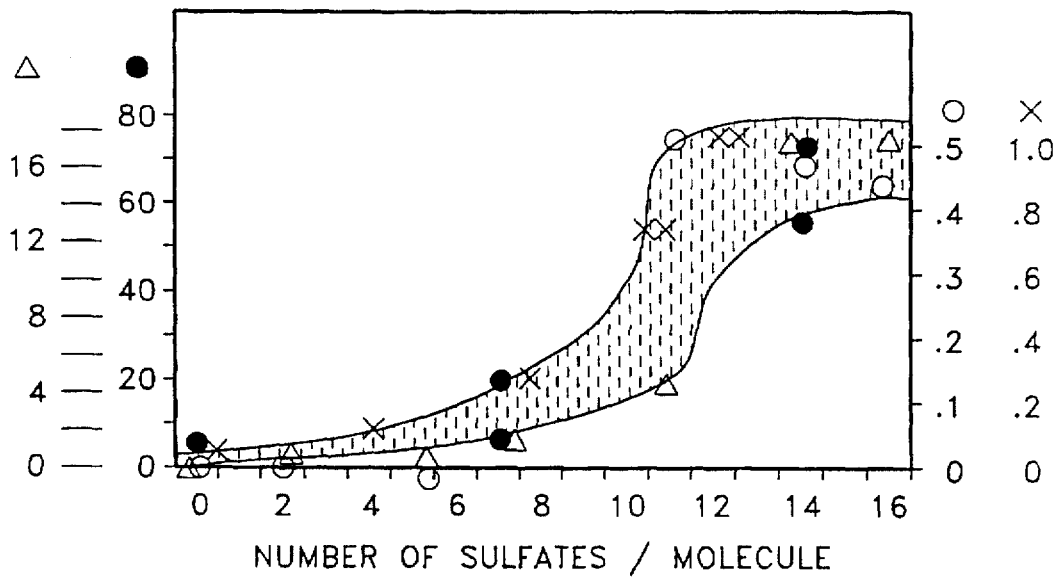
Figure 3B:
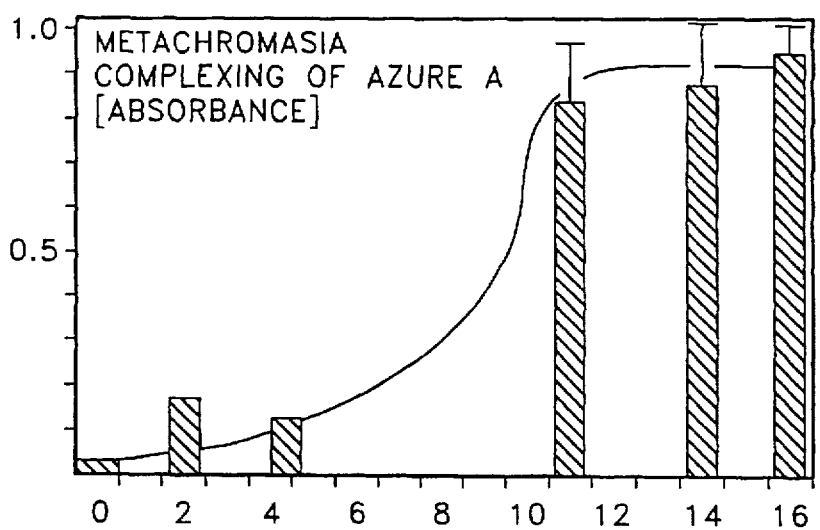

FIG. 3 shows a summary of accumulated data concerning the critical dependence of biological cell modulating activities, based upon the number of anionic (sulfate) groups per molecule of polyanionic CDs, for anti-angiogenesis, endothelial cell growth promotion, smooth muscle-cell growth inhibition, inhibition of virus invasion in T-cells, and optical metachromatic activity which is a biochemical indicator of cell-related biological activity (see A. C. Grant et al, *Anal. Biochem.* 137,25–32,1984), and P. B. Weisz et al, in *Angiogenesis-Key Principles-Science-Technology-Medicine*, Steiner, Weisz, Langer, Ed.s, Birkhaeuser/Springer, 1992).

Figure 4:
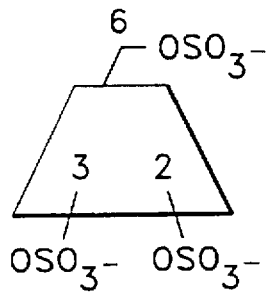
Figure 4:
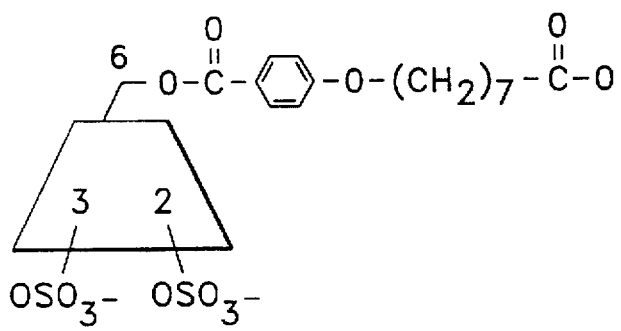

FIG. 4 (A, B, C, D) shows examples of "one-sided" anionic CDs of this invention.

Figure 5B:
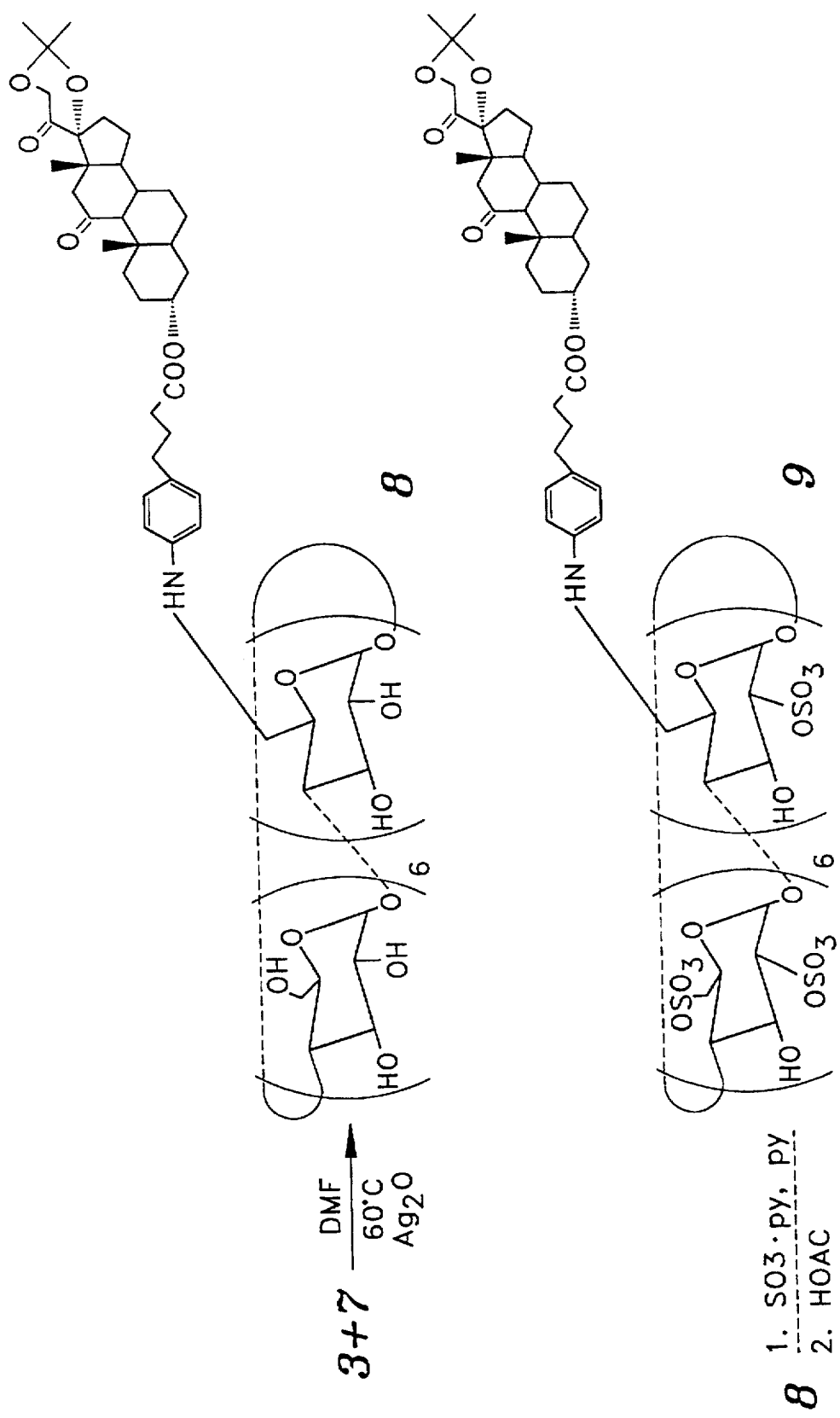

FIG. 5 shows the synthetic steps to obtain a CD-polysulfate with a steroid (hydrocortisone) as a lipophilic and pharmacologically active substituent of the polyanionic CD.

5. DETAILED DESCRIPTION OF THE INVENTION

The present invention provides polyanionic, substituted CD (CD) compounds, having a critical minimum number of polyanionic groups attached. The invention provides for at least 10 anionic groups per CD molecule. Such critically substituted CD compounds have been determined to be suitable for use in multiple therapeutic applications, as discussed further below.

The compounds of the present invention possess cell growth modulating properties similar to heparin, while advantageously lacking heparin's undesirable anticoagulant activity.

With respect to the anionic groups on the CD molecule, these can be the anions of any strong acid. Non-limiting examples of these anions include sulfate, nitrate, sulfonate, and phosphate. Sulfate is preferred.

Furthermore, it has been advantageously discovered that the water solubility of these compounds can be varied from low to intermediate to highly soluble by varying the carbon chain length of a non-polar substituent(s) attached to the polyanionic CD, which substituent is substantially hydrophobic or lipophilic.

By low solubility is meant virtually insoluble or 0 g/100 ml to about 0.5 g/100 ml; by intermediate solubility is meant about 0.5 to about 25 g/100 ml; and by highly soluble is meant a solubility of at least about 25 g/100 ml, preferably at least about 30 g/100 ml. All solubility determinations are carried out at 0° C.

Suitable non-limiting examples of non-polar substituents, which are substantially hydrophobic or lipophilic, include an alkyl, an aryl, an ester, an ether, a thioester and a thioether. These substituents may be varied with respect to the length of their carbon chain to achieve a suitable or desirable water solubility of the polyanionic, substituted CD. By varying the length of the substituent group, one can alter the solubility of the CD molecule, depending upon the desired therapeutic application.

Accordingly, a substituent of hydrophobic chain length greater than about 20 provides a polyanionic, substituted CD of low solubility; a substituent length of from about 7 to about 20 provides a CD of intermediate solubility; and a length of less than about 7 results in a CD, which is highly water soluble. In any regard, it is considered well within the skill of the art to vary the carbon length of the substituent groups for the purpose of achieving the desired water solubility of the CD compounds of the present invention.

With respect to the number of hydrophobic substituents which can be attached to the CD molecule, this number can range from about one to about 14. This provides for the minimum critical number of anions of at least about 10 per CD, and whether the CD is alpha, beta or gamma. For instance, the number of hydrophobic substituents which can be attached can range from about one to about 8 for alpha-CD; from about 1 to about 11 for beta-CD; and from about one to about 14 for gamma-CD.

These CD compounds can be substituted at any available hydroxyl groups of the CD molecule by an anion or non-polar substituent, so long as the minimum critical number of anionic groups of at least ten is provided.

Figure 1:
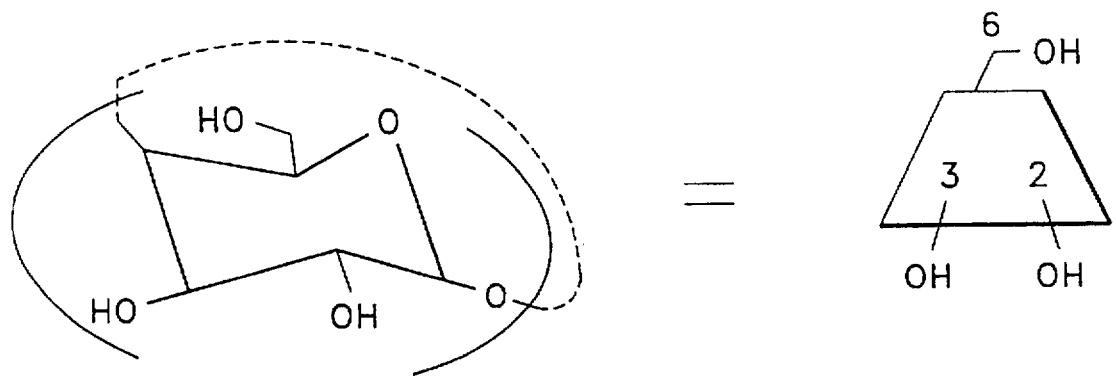
FIG. 1 (A and B) shows a schematic representation of (A) the chemical structure of beta-CD, and (B) the three-dimensional, toroidal structure of same.
Figure 2:
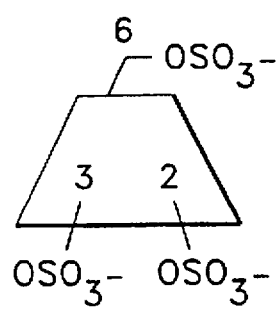
FIG. 2 shows the toroidal representation of anionic (sulfated) CD, in which any of the possible substituent positions (2,3, and 6) carry the anionic (sulfate) substituent.

FIG. 1 depicts the structure of beta-CD (A) and a more three-dimensional view of same which shows its toroidal structure. FIG. 2 illustrates a sulfated CD.

FIG. 3 shows that there is a sharp criticality in the number of anionic (sulfate) groups required for cell modulating activity, namely a requirement for at least about 10 anionic groups. The high density of anionic charges around the CD, while clearly providing a highly desirable cell biological activity, is also likely to generate some limitations of use. Cell and tissue membrane permeability, for example, is known to be inhibited by charge density and favored by a more hydrophobic (lipophilic) character. An entirely ionic compound therefore limits certain aspects of transport in the body, such as penetration into the blood plasma from oral delivery, the penetration of the blood-brain barrier where desired, and so forth. Also there are other desirable biochemical activities resulting from hydrophobic structures, such as affinity for associating with and thereby capturing or transporting other hydrophobes such as cholesterol, carotenes, and others. This invention therefore provides CDs that possess the required critical anionic density, while also possessing hydrophobic (liophilic) portions to advantageously provide these other desirable properties, such as increased blood absorption.

Also as shown in FIG. 3, the compounds of the present invention having a critical minimum number of anionic groups of at least about ten (10) exhibit significant anti-angiogenic activity in combination with hydrocortisone; promotion of endothelial cell proliferation; inhibition of smooth muscle cell proliferation; and inhibition of viral infection of cells by HIV-1.

It is understood that the solubilities of the compounds of the present invention will be altered if hydrophilic groups are introduced onto the hydrophobic chain, as exemplified by FIG. 4D, thereby increasing chain length that would otherwise provide lower solubility.

5.1 CDS with Critical Anion Density and Hydrophobic Substituents

Substituted CDs with critically high anionic group density and additional non-ionic substituents have not been disclosed in prior art, but are described in our U.S. application Ser. No. 07/947,417, now U.S. Pat. No. 5,441,944, which is incorporated herein by reference, wherein non-ionic substituents were recited that included short chain alkyl substituents such as methyl, ethyl, n-propyl, and isopropyl groups, which preserved the substantially high solubility of the sulfated CD, while modifying groups such as ester, ether, thioester, thioether, and carboxylate may add hydrophile activity. The invention provides substituted CDs with critically high anionic group density, and additional non-ionic substituents of sufficiently high hydrophobicity to substantially reduce the water solubility of the hydrophobically-substituted polyanionic CD. Accordingly, the compounds of this invention bear non-ionic substituent groups containing non-polar atom chains (of carbon or sulfur atoms) of at least three atoms, or more, if additional polar modifying groups are also employed as substituents. If the number of non-polar substituents provided is less than will correspond to all hydroxyl positions not substituted by anions, then longer hydrophobic chains would be required. It is therefore more convenient to define the total degree of hydrophobicity provided by the resulting reduction in water solubility achieved. It will therefore be the objective to provide sufficient non-polar substitution to achieve a reduction of water solubility by at least about 30%.

Those compounds of the present invention having low water solubility are particularly suitable for therapeutic applications which call for localization and retention of the compound at a desired site. Such compounds provide for limited dispersion of the compound by diffusion, while advantageously remaining at the site of desired therapeutic treatment.

By way of the present invention, one of skill in the art can lower the solubility of the compounds by covalently bonding hydrophobic substituents to the polyanionic CD molecule.

Another method is by the formation of salts of the anionic species of this invention that have lower or very low solubility. This can be achieved by suitable reactions to exchange the common sodium ion associated with the anions during or after the usual synthesis, with such di- or trivalent metal ions as calcium, magnesium, aluminum, or barium, or others that are physiologically acceptable for the desired therapeutic application.

Another method of lowering the solubility of the compounds of the present invention is by forming much higher molecular weight entities from the monomeric compounds described herein. This can be carried out by oligomerization or polymerization of CD before synthesis of the substituted derivatives. In fact, the polymerization linkage can be achieved by polymer linking agents that contain long chain hydrophobic groups themselves. Methods of polymerizing CD monomers are referenced and recited in U.S. Pat. No. 5,262,404, which is incorporated herein by reference.

5.2 CDS with Critical Anion Density and Hydrophobic Substituents That Add Another Biological Functionality The invention further provides an additional biological functionality to the cell adhesion and cell modulating capability of the polyanionic, substituted CD. This is accomplished by choosing as at least one of the hydrophobic substituents, a compound which is known to have pharmacological activity. Non-limiting examples are steroids, angiostatic steroids, bactericidal, or antibiotic agents, and a variety of other agents such as antioxidants, for example, beta-carotene.

Thus, the addition as a substituent of a steroid such as hydrocortisone provides a compound capable of inhibiting angiogenesis, which substituted compound possesses the heparin-like activity of the CD polysulfate, as well as that of the angiostatic steroid hydrocortisone. An angiostat is understood to be a latent growth inhibitor that by itself possesses no or negligible anti-angiogenic activity, but requires heparin or a heparin-mimic such as the CD-polysulfate to achieve that activity. Other steroidal or non-steroidal structures which are well-known to one of skill in the art may also be employed.

More preferred are those latent growth-inhibiting steroids which lack glucocorticoid and mineralo-corticoid activity, since such activity is an undesired effect, and limits the dose size or extent of use of the steroid for the purpose of the present invention. Among such more preferred steroids are 11 alpha, 17, 21-trihydroxypregn-4-ene-3,20-dione (or 11 alpha-hydrocortisone), 17 alpha, 21-dihydroxypregn-4-ene-3,20-dione (11-desoxycortisol or cortexolone), and 17 alpha, 21-dihydroxypregna-4,9(11)-diene-3,20-dione.

The term "cortisone" and "hydrocortisone" and 11-α isomer of hydrocortisone as used in the present specification and claims are intended to include both the steroids themselves and their derivatives and structural variants thereof.

None of the latent growth-inhibiting steroids themselves effectively inhibits angiogenesis, nor causes regression of tumors in the absence of a highly water-soluble substituted CD sulfate of the present invention associated with a physiologically acceptable cation.

Additionally, any non-steroidal organic compound, which in combination with a substituted CD sulfate associated with a physiologically acceptable cation demonstrates growth inhibiting activity in either of the bioassays described below, can be utilized in the methods of the present invention.

As taught by the present invention, the growth-inhibitory activity of non-steroidal organic compounds is potentiated by combination with a water-soluble substituted CD sulfate associated with a physiologically acceptable cation. Among the non-steroidal growth-inhibiting organic compounds which can be utilized in the present invention are the following: proline analogs such as L-2 azetidinecarboxylic, cis-hydroxyproline, and 3,4-dihydroproline and trans-retinoic acid and other retinoids.

Several well-recognized bioassays have been developed to estimate the angiogenic-inhibiting potency, if any, of a substance. The rabbit cornea is the basis of one of these methods. The cornea is avascular. A small pocket can be made in it, and a tumor implant can be inserted while the rabbit is anesthetized. The tumor is separated from the vascular bed of the host. New capillary blood vessels will grow in a linear manner toward the tumor, and the rate of vessel growth can be measured. For a more detailed description of this assay, see, Gimbrone et al., *J. Nat'l Cancer Inst.* 52:413 (1973) incorporated herein by reference.

A more economic bioassay makes use of the chorioallantoic membrane of the chick embryo. This test will for convenience be referred to hereinafter as the "CAM assay." For a more detailed description of the CAM assay, see Folkman et al., *Science* 221:719 (1983), incorporated herein by reference. A typical CAM assay employs 16 eggs per experiment. A 2 mm diameter disk of methylcellulose containing the test substance is applied to the chorioallantoic membrane of a 6-day chick embryo cultured in a Petri dish in a humidified incubator with 3% carbon dioxide. Two days later (8-day embryo), the membrane is examined under a stereomicroscope at six- to ten-fold magnification. Inhibition of angiogenesis by the test substance is evidenced by the development of an avascular zone around the methylcellulose disc. An avascular zone of 4 mm is graded as (++) and an avascular zone of 2 mm is graded as (+). The potency of the inhibition at the 2 mm and 4 mm zone(s) is expressed as the percentage of the total number of eggs (usually 10) in the test that were rated (++) or (+), i.e., the % of "successes." A rating of zero % reflects absence of inhibition of the test substance under the test conditions.

The sustained release methylcellulose discs are prepared by dispersing appropriate amount(s) of the test substance in an 0.45% aqueous solution of methylcellulose, and depositing 10 microliter aliquots of the resulting solution in a Teflon mold, followed by air drying for about one hour in a laminar flow hood.

A very advantageous feature of the CAM assay is the very high sensitivity of the chick embryo to toxic substances. Moreover, the lack of toxicity of a substance in the CAM assay has been well correlated with lack of toxicity of such substance when administered to other animals.

5.3 "One Sided" CDS with Critical Anion Density

Further, it has now been advantageously and surprisingly discovered by way of the present invention that the above-described polyanionic, substituted CD compounds, wherein the anionic groups are attached substantially solely at the 2- and 3-positions of the CD molecule, unexpectedly possess superior biochemical and pharmacological properties. These are referred to hereinafter as "one-sided" CDs. These "one-sided" CDs are particularly suitable for use in the various therapeutic applications described herein.

The present invention therefore advantageously provides CDs having a critical anion density, which possess cell modulating activity, wherein the anionic substituents, for example sulfates, are located primarily on one side of the CD toroidal structure, while the other side of the toroid possesses largely or entirely non-ionic, non-polar, and preferably hydrophobic substituent groups, if any.

Referring to FIG. 1 and FIG. 2, it should be appreciated that there are certain restrictions on the available number of substituents on either side of the CD-toroid: with beta-CD, there are seven 6-positions on one side and fourteen 2- and 3 positions on the other. It is clear therefore that to achieve a total of at least ten anionic (e.g. sulfate) substituents on the CD molecule, such number can not be accommodated on the 6-position side alone. Most or all of the anions must therefore be placed on the 2- and 3-position side. Accordingly, this invention, when involving "one-sided" polyanionic CD compounds, provides compounds wherein most or all anionic substituents are placed in the 2- and 3-positions. It is to be noted that mere substitution of the 2- or 3- positions alone would yield at most seven anions, far below the critical requirement for cell modulating activity.

The "one-sided" CD compound of this invention also allows flexibility regarding the addition in number and nature of the substituents on the 6-position side, thus providing the ability to alter the degree of hydrophobicity. Hydrophobicity determines the water solubility of the molecule, the ability of interacting with other hydrophobes in solution or on cell or tissue surfaces, the capability of effecting and modulating penetration capabilities of biological membranes, and furthermore the ability to choose as added substituents, compounds that possess an additional pharmacological activity, for purposes and in like manner as previously discussed.

5.4 Inclusion Complexes with CDS of Critical Anion Density

Many years of study involving CDs led to the assumption that any CD having the familiar hollow cavity in its toroidal structure would host guest molecules of suitable size. These inventors also made this assumption at the time of describing in U.S. Pat. No. 5,019,562 (M. J. Folkman and P. B. Weisz) the polyanionic CD, beta-CD tetradecasulfate, to accomplish inhibition of angiogenesis. However, we subsequently discovered that it is not possible to obtain inclusion into the highly polyanionic substituted CD. After consideration of the dimensions and locations of the CD toroidal structure and of the diameter of the anionic substituent groups, it became clear that the anionic groups were located outside at the entrances of the toroidal structure. Their large required number for biological activity together with the large diameter of each group, for example the (—O—SO3) -group, cause the entrances to the cavity to be blocked due to steric hindrance.

The present invention, therefore, unexpectedly provides biologically active CDs having the required critical anion number yet being surprisingly capable of forming inclusion complexes with molecules or portions of molecules that fit the cavity size, and possess sufficient hydrophobicity to attractively interact with the hydrophobic nature of the internal cavity of CD. This is indeed surprisingly accomplished by the "one-sided" anionic CDs of this invention, since these compounds possess the desirable concentration of high density of anions on one side of the CD toroid, while leaving the entrance on the other side unobstructed by bulky anionic groups. This advantageously provides the capability of inclusion complex formation involving such polyanionic CDs with an almost unlimited variety of possible guest molecules having the requisite hydrophobicity. Among the suitable molecules are partially or wholly hydrophobic (lipophilic) organic compounds, such as for example, alkanes, alkenes, aromatics, fatty acids, lipids, terpenes, and biological and pharmacologic agents, such as hydrophobic or partially hydrophobic steroids, vitamins, hormones, antioxidants, such as retinoids, bactericides, antibiotics and antiviral agents, particularly anti-HIV agents such as AZT and ddI, or other nucleoside derivatives.

We have also found that while inclusion of molecules of pharmacological interest into the polyanionic CD of the prior art is unattainable, an inclusion complex can be created by way of the present invention. For example, we thereby succeeded in obtaining the internal complex between cortisone and sulfated CD, as shown by spectroscopic absorption of the product.

5.5 Multiple Biological Functions Possessed by Compounds and Compositions

The compounds and compositions of this invention advantageously possess multiple biological functions and pharmacological activities as compared with CD compounds including the sulfated (polyanionic) compounds of the prior art.

Accordingly, the compounds and compositions of the present invention are especially suitable for use in the therapeutic methods described below in section 6.

The polyanionic CDs, like heparins, form external electrostatic complexes between their negative anions and the multiple cationic (basic) groups on proteins, such as the growth factor proteins, also known as heparin binding growth factors (HBGFs). They are, as noted by us, "heparin mimics." As a result, polyanionic CDs bind, as is the case of the heparins, to proteins and surface proteins, thereby binding to cell and tissue surfaces by virtue of their strong electrostatic forces.

By addition of substantially hydrophobic substituents, the CDs of this invention can also interact with other biologically significant lipophile groups. By providing added hydrophobic groups that are themselves pharmacologically active, novel pharmacological properties are further provided.

By providing the anionic group on only one side of the CD toroidal structure ("one-sided" anionic CDs), we provide, in addition to the existing electrostatic binding capacity due to the high anion density, the capability of generating inclusion complexes with other agents, which agents can thus be more efficiently solubilized, stabilized, and delivered than heretofore accomplished. While delivery by use of CD inclusion complexes per se is a widely developed art, the compounds of this invention advantageously combine the properties of strong adsorption on cells and tissues, thereby surprisingly enhancing direct delivery capabilities beyond merely relying on desorption of the guest molecule and diffusion to target surfaces. Many variants in methods of application and adaptation to different tasks of therapy or biotechnology are thereby enabled, as discussed hereinafter.

6. Applications and Methods of Use

The compounds of the present invention are especially useful in a multiple number of pharmacological and medical applications. These constitute significant improvements in applications previously described such as the use of anionic CDs to modulate cell growth behavior. By the addition and choice of hydrophobic substituent, there are provided methods of treatment allowing for improved efficiency of delivery of the therapeutic compounds of the invention to tissues, organs, and body parts. A change in balance of hydrophobic (lipophilic) and hydrophilic (ionic) properties of the CD compounds of this invention can favorably alter biological membrane permeation, with the consequence of improving sorption into blood plasma by way of oral delivery. The compounds of the invention furthermore alter interaction and retention by different biochemical components of cells, tissues, organs and body parts, such as with or on fatty components, lipids, and other lipophilic materials. The methods of treatment can thus be adapted to specific needs of the type and specific pathology involved.

The compounds of the present invention advantageously possess the pharmacological activity of modulating cellular proliferation in a number of therapeutic applications.

It is believed, for example, that the application of compounds of this invention to cardiovascular pathologies is beneficial. Heparin has been shown to possess beneficial lipolytic activities (see A. C. Asmal et al, *Brit. J. Clin. Pharmacology* 7, 531–533, 1979), but its anticoagulant activity precludes its use in sufficiently high dosage. The new and improved "heparin mimics" of this invention, devoid of such anticoagulant activity, overcome this problem.

It has been noted that proliferation of human smooth muscle (smc) cells is promoted by lipoprotein (see D. J. Grainger et al, Science 260, 1655–1658, 1993). In relation to methods of inhibiting smc proliferation, inhibiting plaque enlargement, or preventing restenosis after angioplasty, the present invention provides the use of the modified CD polyanionic compounds, preferably the polysulfates. The compounds provide additional benefits by impacting on plaque and other areas of cardiovascular injury by optimal attachment to such areas of plaque and removal of plaque by lypolytic or dissolution mechanisms.

The present invention therefore provides methods of treatment of cardiovascular disorders. These methods include inhibiting restenosis after angioplasty and reducing blood lipids. The methods using sufficient numbers and lengths of hydrophobic (lipophilic) substituents linked to the critically sulfated or other heavily anionic CD are especially useful for these purposes.

Particularly preferred for use in the methods of the invention are "one-sided" anionic CDs. It has already been demonstrated that the ordinary beta-CD cavity is capable of lowering cholesterolemia in mammals (see M Riottot et al, Lipids 28,3,181–188,1993). However, it is well-known that CDs have very limited solubility of a few milligrams per milliliter and are hemolytic at near 5 mg/ml concentration. On the other hand, addition of the anionic groups to the CD molecule removes this hemolytic activity (see P. B. Weisz et al, Biochem. Pharm. 45, 1011–1016, 1993).

The present invention further provides methods to inhibit proliferation of endothelial cells, the generation of endothelium and the generation of new vascular systems, capillaries or blood vessels. These processes are known as neovascularization. It is therefore concerned with methods of preventing or inhibiting neovascularization or angiogenesis. The therapeutic use of the compounds of this invention provides improved effectiveness of such treatments by optimizing absorption or targeting, as discussed above. The methods employ compositions that comprise the polyanionic CDs of the present invention, along with an additional angiostatic agent of the type previously discussed.

The present invention furthermore provides methods of improved anti-angiogenic treatments by delivering the anti-angiogenic compound in a more intimate form than by an independent compound in a composition. In one embodiment, the angiostatic compound, being hydrophobic, such as an angiostatic steroid, is covalently linked to the polyanionic CD as the hydrophobic substituent, or as one of the hydrophobic substituents of the compound of this invention. In another embodiment, the hydrophobic or partially hydrophobic angiostatic molecule is combined with the "one-sided" polyanionic CD to form the inclusion complex of the present invention. As noted above, random attachment of the sulfate groups on the CD molecule has proven to disadvantaegously eliminate internalization of molecules by inclusion complexation with the CD. The present invention addresses this problem by providing the "one sided" anionic, such as sulfated, CDs which leaves one door open, so-to-speak, for internalization (inclusion complexation). Both embodiments provide uniformly dosed proportions of the anionic CD of the present invention and the angiostat of interest. This is particularly useful in the preparation and use of these angiostatic compounds such as steroids that have very limited water solubility. The compounds of this invention now unexpectedly make solubilization of hydrophobic therapeutic agents possible by inclusion complexation.

Another aspect of the invention provides methods of treatment in the area of oncology. While not wishing to be bound by any particular theory, it is believed that treatment with the composition of the present invention inhibits the creation of new capillaries necessary for tumor growth. This results in the tumor having an insufficient supply of essential nutrients. Thus, tumors in mammals, including humans, when treated in accordance with the present invention, do not grow and may even die. Among the tumors contemplated as responsive to the composition and methods of this invention are Reticulum Cell Sarcoma, Lewis Lung Carcinoma, B-16 Melanoma, and Bladder Carcinoma, as well as others.

Neither mature non-growing blood vessels nor mature non-growing vascular tissue appear to be affected by treatment with the compositions of the present invention. Inhibition of angiogenesis in accordance with the present invention, in addition to its effect upon tumor regression and metastasis in tumor-bearing animals, may be effective in treating a number of other ailments, as described hereinafter.

The present invention further provides a method for treatment of a number of other non-tumorous disorders which are characterized by pathological cell or tissue growth, including angiogenesis. Thus the invention provides a method for treatment of mammals, including humans, afflicted with a number of non-neoplastic pathological conditions including rheumatoid arthritis, in which abnormal capillary growth can destroy joint cartilage; hemangiomas, in which abnormal capillary proliferation appears in newborns and can persist for up to 2 years; angiofibromas which develop in the nasopharynx; psoriasis, in which excessive proliferation and shedding may be dependent on abnormal capillary growth in the dermis. Additionally, the present invention provides a method for treatment of a number of ophthalmological pathologies which are associated with undesired angiogenesis, including diabetic retinopathy, retrolental fibroplasia and neovascular glaucoma.

It is a further purpose of this invention to provide methods for treatments wherein it is desired to promote rather than to inhibit cellular growth, cellular proliferation, or tissue or vessel repair or production. Thus, the compounds of the present invention can also positively modulate cellular proliferation. This is the case of wound healing and repair of damage to tissue and body parts due either to injury or surgical procedures, as well as deterioration or loss of structures due to pathology.

In all such cases, it is desired to have methods for delivering, and preferably for optimal targeting, of proteinic growth factors to the location of the desired repairs.

For these purposes, the polyanionic CDs of this invention are combined with a suitable proteinic growth factor to form a composition suitable for wound healing. The polyionic CD, when contacted with a fluid medium containing the growth factor protein, e.g. (HBGF), for a sufficient amount of time, produces an electrostatic (external) complex. Such a complex is suitable as the composition to be delivered to the site of injury. It is significant to note that electrostatic complexation, as in the case with heparin, is also known to stabilize the proteinic molecule against enzymatic degradation which may otherwise result. Delivery of the complex will therefore not only provide a convenient method of delivery of a therapeutic agent directly to cell and tissue, but will also advantageously enhance the half-life and bioavailability of growth factor protein delivered as a protected electrostatic complex.

Dosages of the compounds or compositions of the present invention, as well as methods of their administration, are described in detail in U.S. Pat. Nos. 5,019,562 and 5,183,809, which patents are incorporated herein by reference. It is considered well within the skill of the art to routinely determine the appropriate amounts and mode of administration of the compounds of the invention.

7. Methods of Making the Compounds of the Invention

In order to arrive at the CD compounds of the present invention having at least about ten anionic, e.g. sulfate groups per molecule, the method of the invention utilizes the CD positions 2-, and 3-, inasmuch as there are only seven 6-positions available. Also, for the "one-sided" anionic substitution of critical anion density of ten or greater anions, such synthesis must entail all or nearly all anion additions to the 2,3-side. Furthermore, addition in such number on only the 2,3-side requires utilization of both the 2- and 3-positions for anion addition, inasmuch as there are only seven of each available. The discussion and examples are based on the use of beta-CD. It is noted that the limitation of ten required anions will not change these restrictions on methods of addition for alpha-CD, where there exist only six of each of the 2-, 3, 6-positions, or for gamma-CD where there exist eight of each. While, for this invention, the use of beta-CD is preferred, particularly beta-CD tetradecasulfate, over utilization of alpha- or gamma-CD, the discussion of this form of CD shall not be construed as limiting this invention to the beta form of CD. Alpha- and gamma-CD are also adaptable to and considered suitable for practice in the present invention, particularly if such forms adequately suit the purpose of one of skill in the art.

To achieve critical sulfation as well as addition of substantial hydrophobic substituents, a general method is provided as follows.

The compounds of the present invention can be synthesized under conditions which allow for hydrophobic substitution at the 2-, 3- or 6-positions of CD. The only limitation being that there is provided the minimum critical number of anionic groups of at least about 10 at these positions. The preferred anionic group is sulfate. One may also choose for the hydrophobic chain to be added, one which will not include any reaction centers that will react with a sulfating agent. The product, after purification if needed, can be reacted with a sulfating agent at sufficient severity (concentration, time, temperature) to achieve sulfation of at least about ten secondary hydroxyl units.

The sulfating agent is typically one of the following: the sulfur trioxide complex of pyridine, chlorosulfonic acid, sulfur trioxide complex of trimethyl amine. Sulfating is accomplished in a non-protic solvent, such as dimethyl formamide, pyridine, or dimethylsulfoxide.

In order to obtain a strictly "one sided" polyanionic CD product, and since the primary hydroxyl group on the 6-position of the sugar units is generally the most reactive, one can react and ultimately substitute a desired hydrophobic compound only at these hydroxyl groups under mild enough reaction conditions so as to leave the secondary (2-, and 3-position) hydroxyl groups unreacted. Also, for these hydrophobic substituents, one chooses a hydrophobic chain product which will not include any reaction centers that will react with the subsequently used sulfating agent. The so substituted CD product, after purification, is reacted with a sulfating agent at sufficient severity (concentration, time, temperature) to achieve a minimum critical sulfation of at least about ten of the secondary hydroxyl units. The sulfating agent and solvent are as described above.

The following examples are provided to illustrate this invention. However, they are not to be construed as limiting the scope of the invention in any manner whatsoever.

8. EXAMPLES

Example 1

CD with more than 10 sulfate groups and thioethyl group substitutions as hydrophobic components. Compound A. This is represented in FIG. 3, where R=—S—CH$_2$—CH$_3$.

The compound heptakis(6-ethanesulfide-6-deoxy)-beta-CD polysulfate was produced as follows: 8.64 g of dry beta-CD was added to a stirred solution of 42 g of triphenylphosphine (TPhP)and 8.2 ml of bromine in 160 ml dimethyl formamide (DMF). The mixture was stirred for 16 hours at 83° C., concentrated by evaporation to one third is volume, its pH adjusted to 9.5 by the addition of 3M NaOMe in methanol (65 ml), with external cooling, stirred at room temperature for 1 hour to decompose esters, and poured into ice water. Precipitate was washed in water, redissolved in DMF, reprecipitated in methanol and washed in 3×1.5 l of methanol to produce the product of heptakis(6-bromo-6-deoxy)-beta-CD (Int.1). 1.45 g of dry sodium hydride in 100 ml of DMF, stirred at 0° C. under nitrogen was added to 4.8 ml of ethanethiol. To this solution, after stirring 30 minutes, was added a solution of 2.4 g of Int.1 in 35 ml DMF, at 0° C. for 7 hours. After 40 hours at room temperature unreacted ethanethiol was removed, reduced to ¼ its volume And precipitated in 600 ml of water. The white precipitate, heptakis(6-ethanesulfide-6-deoxy)-beta-CD (Int.2) was washed twice with methanol.

To a solution of 0.7 g of Int.2 in 35 ml dry pyridine was added 3.2 g of sulfur trioxide pyridine complex., and reacted at 25° C. for 3 days. Pyridine was evaporated to precipitate a solid, and 30 ml of 10% sodium acetate solution was added. The mixture was stirred one hour, then methanol (250 ml) was added to form a suspension. The methanol was largely evaporated on a rotary evaporator. 250 ml of ethanol produced a precipitate, which precipitate was allowed to settle, and then washed in additional 100 ml of ethanol. The solid was chromatographed on Sephadex with water as the eluant. A fraction of 0.7 g of melting point of ca. 205°–210° C. was obtained, given an elemental sulfur analysis of 21.77 wt. %, which corresponds to the product heptakis96-ethanesulfide-6-deoxy)-beta-CD polysulfate with about 12 sulfate groups, corresponding to the compound of FIG. 3, with R=—S—$CH_2$—$CH_3$ linked to the 6-position primary C atom, thus producing a hydrophobic chain element of four atoms. This compound is also a "one-sided" anionic polyanionic CD.

Example 2

CD with more than 10 sulfate groups and thiooctyl group substitutions as hydrophobic components.Compound B. This compound is represented by FIG. 3, with R being —S—$(CH)_7$—$CH_3$—.

The compound heptakis(6-octanesulfide-6-deoxy)-beta-CD polysulfate was produced as follows:

To a solution of 0.62 g of dry sodium hydride in 100 ml of DMF, stirred at 0° C. under nitrogen was added, dropwise, 4.1 g of loctanethiol. To this solution, after stirring 30 minutes, was added, gradually, 3.14 g of Int.1, stirred at room temperature for 50 hours and poured into 1 liter of methanol. The yellow precipitate was collected by filtration, washed in water (2×300 ml) and in methanol (2×200 ml) and dried in vacuo, affording 3.8 g of heptakis(6-octanesulfide-6-deoxy)-beta-CD (Int.3).

For crystallization, 0.12 g was dissolved in DMF and diluted methanol, after two days producing colorless crystals of m.p. 238°–240° C.

To a solution of 2.03 g of Int.3 in 700 ml pyridine was added 6.36 g of sulfur trioxide pyridine complex and stirred at 100° C. for 18 hours. Pyridine was evaporated to precipitate a solid, which was dissolved in 60 ml of 10% sodium acetate solution and stirred for one hour. This solution was added to methanol (500 ml). The precipitate was washed in ethanol (2×20 ml). The precipitate afforded 5.4 g of raw product containing heptakis(6-octanesulfide-6-deoxy)-beta-CD polysulfate. A fraction after Sephadex 25 chromatography yielded a product with sulfur analysis of 16.64 5 which indicates the presence of about 11 sulfate groups. This corresponds to the compound of FIG. 3, with R=—S—$(CH_2)_7$—$CH_3$ linked to the 6-position primary C-atom, thus producing a hydrophobic chain element of ten atoms. This compound is also a "one-sided" anionic polyanionic CD.

Example 3

CD with more than 10 sulfate groups and thiopentyl group substitutions as hydrophobic components. Compound C. This compound is represented by FIG. 4.

The compound heptakis(6-pentanesulfide-6-deoxy)-beta-CD polysulfate was produced in a strictly analogous fashion as example 5, with pentylthiol taking the place of ethyl thiol and octylthiol of examples 4 and 5, respectively. The product of this reaction corresponds to the compound of FIG. 3, with R=—S—$(CH_2)_4$—$CH_3$ linked to the 6-position secondary C-atom, thus producing a hydrophobic chain element of seven atoms. This compound is also a "one-sided" anionic polyanionic CD.

Examples 1, 2, and 3 illustrate compounds of this invention with varying amounts of hydrophobicity accomplished by substituents of varying length of non-polar bonding atom groups. It is possible to have incorporation of side chains with only portions of only them comprising chains of non-polar atom groups. Such compounds would be expected to have hydrophobicity expressed in that portion of the environment, that is on a molecular scale, although the overall molecule may exercise less average hydrophobicity in tests such as solubility of the entire molecule. An example is the structure of D in FIG. 4, which was obtained in a multistep synthesis described in Example 6.

Example 4

Heptakis[6-hepta-O-(4-carboxyphenyloxy) octanoate)]-beta-CD Polysulfate. Compound D, FIG. 4.

In its side chain this compound contains more than 10 sulfate groups and complex substituents, containing a 12-member chain of non-polar atoms, but terminated by a polar group.

Benzyl 8-bromooctanoate (Int.4) was produced from dicyclohexylcarbodiimide and bromooctanoic acid, in 4-(dimethylamino)pyridine. Independently, allyl-hydroxybenzoate (Int.5) was produced from DBU, allyl bromide and 4-hydroxybenzoic acid, in acetonenitrile. Benzyl 8-[4-(allyloxycarbonyl)phenyloxy]-octanoate (Int.6) was then produced by reducing (Int.5) in dry DMF and subsequently reacting the product with (Int.4) in dry DMF. A 0° C. solution of (Int.6) was reacted in dichloromethane with pyrrolidine in the presence of triphenylphosphine and tetrakis(triphenylphoshine)palladium to yield benzyl 8-(4-carboxyphenyloxy)octanoate (Int.7).Independently beta-CD was reacted with tert-butyldimethylsilane chloride in pyridine to produce heptakis(6-0-tert-butyldimethylsilyl)-beta-cyclodextrin (Int.8). This product was reacted with benzylbromide and sodium hydride in anhydrous DMF to produce heptakis(2,3-Otetradecabenzyl-6-0-hepta-tert-butyldimethylsilyl)-beta-cyclodextrin (Int.9). Benzylation of all 2- and 3-hydroxy groups is achieved by reaction with benzyl bromide and sodium hydride in DMF, followed by removal of the silyl protecting groups by refluxing with tetrabutylammonium fluoride in THF, the organic phase washed, dried, and concentrated yielding heptakis(2,3-Otetradecabenzyl)-beta-CD (Int.10). The condensation reaction of Int.10 with Int.7 was carried out using the classical DCC-DMAP treatment for more than 30 hours, followed by purification on silica gel, and hydrogenation in ethanol over Pd/activated carbon, affording heptakis[—O—(4-carboxyphenyloxy octanoate)]-beta-CD (Int.11). This final intermediate was sulfated by the standard sulfation procedure to yield the product of FIG. 4D. Elemental analysis indicated that sulfation to approximately 14 sulfate groups was achieved. The product was shown to have inhibitory activity on rat smooth muscle cell proliferation by thymidine uptake assay in vitro.

The variation of homopolar property contributions of the products made by choice of the composition of the substituents attached to the 6-position of the critically sulfated CD, requiring ten or more sulfate groups occupying sites of the 2- and the 3-position of the sugar units was determined by the comparative solubilities of such compounds as compared to the ordinary CD polysulfide of the prior art which was lacking hydrophobic substitutions.

Example 5

Aqueous solubilities of beta-CDs observed were as follows:

| Compound | number of carbon or sulfur atoms in chain | solubility 27° C. | (g/100 ml) 0° C |
|---|---|---|---|
| CD | 0 | ca. 1 | less than 1.0 |
| CDS | 0 | ca. 127 | ca. 95 |
| A | 3 | 66 | 52 |
| C | 6 | ca. 58 | 25 |
| B | 9 | 11.3 | 8.2 |

CD is unsulfated beta-CD
CDS is CD polysulfate of the prior art

It is noted that by providing a pre-determined length of hydrophobic substitute chain, a desired solubility reduction can be obtained. In this case, agents of solubilities above about 20 to 30 g/100 ml (measured at 0° C.) are achieved below chain lengths of below about seven; solubilities below about 20 g/100 ml are therefore attained with chain lengths above seven or eight. Further lengthening of such chains in the hydrophobic substituents can, of course, be routinely accomplished. Very low solubilities will be achievable with chain lengths of 20 or more hydrophobic atom units, providing solubilities estimated at by about 0.2 g/100 ml or less. For negligible solubilities, one can synthesize oligomers or polymers containing such units as taught by this invention.

Example 6

It was important to ascertain that the addition of a hydrophobic group to CDs does not interfere with or destroy the cell biological activity of CDS. The compound with the most hydrophilic (lipophilic) group above, namely compound B, having octyl groups, and in fact as many as seven such chains, on the molecule was tested for its activity to inhibit the growth (proliferation) of smooth muscle cells (smc). The assay is that previously used by some of us (see H. C. Herrmann et al, *Arteriosclerosis and Thrombosis* 13, 924, 1993). It is described briefly, with the resulting observations, in the following example.

Example 7

Human umbilical vein smc were allowed to attach to fibronectin coated 96 well microliter plates, incubated for 72 hours with varying concentrations of the CD test sample and 10% fetal calf serum. Cells were fixed, stained with naphthol blue-black, lysed, and quantitated by light absorption at 530 nm. $ID_{50}$ is the test sample concentration that results in half-maximal inhibition of proliferation.

| Sample | $ID_{50}$ (mg/ml) |
|---|---|
| CDS | 1.0 ± 0.2 |
| B | ca. 0.1 to 1.0 |

It was evident that the highly substituted sample was at least as active as, with strong evidence for considerably higher activity than the CD polysulfate of the prior art. It should be noted that a smaller $ID_{50}$ corresponds to correspondingly lower dose requirement to achieve the same inhibitory effect. Also it should be noted that the total number of hydrophobic (lipophilic) atomic groups placed on sample B was actually approaching 8 (chain C) times 7 (number of substituents added at position -6) or a total of fifty-six, or if we count the S atom and the secondary C atoms in the entire chain, we are dealing with a total of 60 non-polar groups having been added without interfering, and, in fact, increasing the biological activity of the CD polysulfide.

The invention provides "one-sided" polyanionic CD having a critical number of anionic substituents. These "one-sided" CDs freely admit guest molecules into the internal cavity for complexation. This provides the resultant multiple potential for pharmacological storage and delivery of guest molecules. The following examples will illustrate such capability of compounds of this invention, in contrast to the CDS composition of the prior art.

Example 8

When the water phase containing compound A was contacted with toluene and subsequently examined for UV absorption in the UV band of absorption by the benzene ring, the molar amount of toluene found approached that of the CD-compound A contained. The same result was observed when compound C was similarly tested. In contrast, repetition of the test with unsubstituted CDS of the prior art showed no UV evidence of toluene associated with that compound.

Example 9

2.3 mM of the "one-sided" CDS sample of example 4 was contacted with a suspension of 2.9 mM of a steroid, 19-norandrost-4-ene3,17-dione. A shift of the adsorption maximum from 244 to 240 nm was observed, indicating formation of the inclusion complex. Such shift could not be observed with ordinary CDS of the prior art.

The following example describes the generation of a polysulfated CD with hydrophobic (lipophilic) substituent or substituents that have pharmacological activity themselves. It deals with a method of producing a linked hydrocortisone-CD polysulfate, thus combining the two activities required for anti-angiogenesis activity: a heparin-mimic and an angiostat.

Example 10

The preparation of a covalently linked beta-CD-hydrocortisone was begun with treatment of the CD with tosyl chloride in pyridine to obtain the monotosylate at 6-position of CD (2 in FIG. 5). Displacement of the tosylate group with sodium iodide at 95° C. for 3 hours in the dark yielded compound 3 in FIG. 5. Independently, hydrocortisone (5β-pregnane-3α,17α, 20-triol, 11,20dione) was protected with 2,2-dimethoxypropane in DMF, at 60° C., to obtain 5β-pregnane-3α-ol,17α,20-acetonide,11,20-dione (compound 4 in FIG. 5). The side chain was prepared by protecting 4-(4aminopheny)butyric acid with a Z group to give the corresponding 4-(4-carbobenzyloxy-aminophenyl) butyric acid (5 in FIG. 5). The condensation between compound 4 and 5 was achieved in DMF at room temperature, in the presence of DCC and DMAP for 19 hours, and the product purified by silica gel chromatography to afford compound 6 in 67% yield, followed by hydrogenation over palladium on activated carbon to provide 1-hydrocortisone-4-(4-aminophenyl)butyric acid ester (compound 7 in FIG. 5). The covalent linking of compound 4 with compound 7 was achieved by reaction in DMF at 60° C. for 48 hours to obtain the hydrocortisone-CD linkage, compound 8. This compound is subjected to sulfation as shown in the last step of FIG. 5.

Similar and other steroids may be linked to the CD structure. Variants, improvements and simplification in the synthetic steps are possible and may be achieved by the skilled person in the art of organic synthesis.

It is to be understood that the foregoing detailed description and accompanying examples are merely illustrative and are not to be taken as limitations upon the scope of the invention, which is defined solely by the appended claims and their equivalents. Various changes and modifications, including without limitation, those relating to the substituents, derivatives, syntheses, formulations and/or methods of use of the invention, may be made without departing from the spirit and scope of the present invention.

What is claimed is:

1. A substituted "one-sided" polyanionic cyclodextrin compound wherein at least about ten substituents per cyclodextrin molecule are anions of a strong acid selected from the group consisting of sulfate, nitrate, sulfonate and phosphate, said compound being associated with a physiologically acceptable cation, at least most of said anions being located at the 2- and 3-positions of said cyclodextrin, and at least one hydrophobic substituent including a chain of at least three atoms, wherein each one of said three atoms is selected from the group consisting of a carbon atom and a sulfur atom, said hydrophobic substituent being located at at least one of the 6- positions of the cyclodextrin.

2. The substituted "one-sided" polyanionic cyclodextrin compound of claim 1, wherein said hydrophobic substituent is selected from the group consisting of alkyl, aryl, ester, ether, thioester and thioether.

3. The substituted polyanionic cyclodextrin compound of claim 2, wherein at least one of the number and the length of the hydrophobic substituent is sufficient to reduce water solubility of the polyanionic cyclodextrin compound by at least thirty percent.

4. The substituted polyanionic cyclodextrin compound of claim 2, wherein at least one of the number and the length of the hydrophobic substituent is sufficient to increase absorption of said cyclodextrin compound into the blood stream of a mammal upon oral administration.

5. The substituted polyanionic cyclodextrin compound of claim 1, wherein at least one of the hydrophobic substituents is pharmacologically active.

6. The substituted polyanionic cyclodextrin compound of claim 5, wherein the pharmacologically active substituent has angiostatic, antiviral or antibiotic activity.

7. The substituted polyanionic cyclodextrin compound of claim 6, wherein the pharmacologically active substituent is an angiostat.

8. The substituted polyanionic cyclodextrin compound of claim 7, wherein the angiostat is a steroid.

9. An inclusion complex of a substituted "one-sided" polyanionic cyclodextrin of claim 1 and a guest molecule possessing a hydrophobic structure capable of penetration into and complexing with the cyclodextrin.

10. The inclusion complex of a substituted "one-sided" polyanionic cyclodextrin of claim 9, wherein said guest molecule is a pharmacologically active compound.

11. The inclusion complex of claim 10, wherein said guest molecule is selected from the group consisting of an alkane, an alkene, an aromatic, a fatty acid, a lipid, a terpene, a steroid, a vitamin, a hormone, an anti-oxidant, a retinoid, a bactericide, an antibiotic, an antiviral agent, the anti-HIV agent AZT, the anti-HIV agent ddI, and a nucleoside derivative.

12. A method of producing a sulfated inclusion complex which comprises the steps of 1) forming an inclusion complex by contacting a polyanionic cyclodextrin with a guest molecule possessing a hydrophobic structure capable of penetrating into and complexing with said cyclodextrin, and 2) sulfating said polyanionic cyclodextrin to yield said sulfated inclusion complex wherein at least about ten substituents per cyclodextrin molecule are anions of a strong acid selected from the group consisting of sulfate, nitrate, sulfonate and phosphate.

13. The method of claim 12, wherein said guest molecule is a steroid.

14. An inclusion complex obtained by the method of claim 12.

15. The inclusion complex of claim 14, wherein said guest molecule is a steroid.

16. The inclusion complex of claim 15, wherein the steroid is hydrocortisone.

17. The inclusion complex of claim 14, wherein said guest molecule is an antiviral molecule.

18. The inclusion complex of claim 17, wherein the antiviral is AZT.

19. The inclusion complex of claim 14, wherein said guest molecule is a retinoid.

20. A method of producing a sulfated inclusion complex which comprises the steps of 1) forming an inclusion complex by contacting a polyanionic cyclodextrin with a guest molecule possessing a hydrophobic structure capable of penetrating into and complexing with said cyclodextrin, and 2) sulfating said polyanionic cyclodextrin to yield said sulfated inclusion complex wherein at least about ten substituents per cyclodextrin molecule are anions of a strong acid selected from the group consisting of sulfate, nitrate, sulfonate and phosphate and further wherein said polyanionic cyclodextrin has at least one hydrophobic substituent containing a chain of at least three atoms, wherein each of said three atoms is selected from the group consisting of a carbon atom and a sulfur atom.

21. The method of claim 20, wherein said guest molecule is a steroid.

22. An inclusion complex obtained by the method of claim 20.

23. The inclusion complex of claim 22, wherein said guest molecule is a steroid.

24. The inclusion complex of claim 23, wherein said steroid is hydrocortisone.

25. The inclusion complex of claim 22, wherein said guest molecule is an antiviral molecule.

26. The inclusion complex of claim 25, wherein said antiviral molecule is AZT.

27. The inclusion complex of claim 22, wherein said guest molecule is a retinoid.

28. A method of producing a sulfated inclusion complex which comprises the steps of 1) forming an inclusion complex by contacting a "one-sided" polyanionic cyclodextrin with a guest molecule possessing a hydrophobic structure capable of penetrating into and complexing with said cyclodextrin, and 2) sulfating said polyanionic cyclodextrin to yield said sulfated inclusion complex wherein at least about ten substituents per cyclodextrin molecule are anions of a strong acid selected from the group consisting of sulfate, nitrate, sulfonate and phosphate, at least most of said anions being located at the 2- and 3- positions of said cyclodextrin, and further wherein said polyanionic cyclodextrin has at least one hydrophobic substituent containing a chain of at least three atoms, wherein each one of said three atoms is selected from the group consisting of a carbon atom and a sulfur atom.

29. The method of claim 28, wherein said guest compound is a steroid.

30. An inclusion complex obtained by the method of claim 28.

31. The inclusion complex of claim 30, wherein said guest molecule is a steroid.

32. The inclusion complex of claim 31, wherein said steroid is hydrocortisone.

33. The inclusion complex of claim 30, wherein said guest molecule is an antiviral molecule.

34. The inclusion complex of claim 33, wherein said antiviral molecule is AZT.

35. The inclusion complex of claim 30, wherein said guest molecule is a retinoid.

36. The substituted polyanionic cyclodextrin compound of claim 2, wherein said hydrophobic substituent comprises at least seven atoms, wherein each one of said seven atoms is selected from the group consisting of a carbon atom and a sulfur atom.

37. The substituted polyanionic cyclodextrin compound of claim 2, wherein at least one of the number and the length of the hydrophobic substituent is sufficient to reduce water solubility of the polyanionic cyclodextrin compound at 0° C. to a value between 0.2 and 30 g/100 ml.

* * * * *